(12) United States Patent
Hedges et al.

(10) Patent No.: US 7,323,438 B2
(45) Date of Patent: Jan. 29, 2008

(54) CLEANSING ARTICLE WITH IMPROVED HANDLEABILITY

(75) Inventors: Steven Kirk Hedges, Fairfield, OH (US); Edward Dewey Smith, III, Mason, OH (US)

(73) Assignee: Procter & Gamble, Cincinnati, OH (US)

( * ) Notice: Subject to any disclaimer, the term of this patent is extended or adjusted under 35 U.S.C. 154(b) by 536 days.

(21) Appl. No.: 10/863,433

(22) Filed: Jun. 8, 2004

(65) Prior Publication Data

US 2004/0254086 A1 Dec. 16, 2004

Related U.S. Application Data

(60) Provisional application No. 60/478,631, filed on Jun. 13, 2003.

(51) Int. Cl.
*C11D 17/00* (2006.01)
(52) U.S. Cl. ..................................... 510/438
(58) Field of Classification Search ............... 510/438, 510/439, 440
See application file for complete search history.

(56) References Cited

U.S. PATENT DOCUMENTS

| | | | |
|---|---|---|---|
| 4,203,857 A | 5/1980 | Dugan | |
| 4,866,806 A | 9/1989 | Bedford | |
| 5,110,843 A * | 5/1992 | Bries et al. | 521/159 |
| 5,217,663 A | 6/1993 | Seville | |
| 5,771,524 A | 6/1998 | Woods et al. | |
| 6,217,889 B1 | 4/2001 | Lorenzi et al. | |
| 6,267,975 B1 | 7/2001 | Smith, III et al. | |
| 6,322,801 B1 | 11/2001 | Lorenzi et al. | |
| 6,428,799 B1 | 8/2002 | Cen et al. | |
| 6,451,331 B1 * | 9/2002 | Slavtcheff et al. | 424/404 |
| 6,491,928 B1 | 12/2002 | Smith, III | |
| 6,491,933 B2 | 12/2002 | Lorenzi et al. | |
| 6,503,526 B1 | 1/2003 | Krzysik et al. | |
| 6,508,602 B1 | 1/2003 | Gruenbacher et al. | |
| 6,541,533 B2 | 4/2003 | Kogure et al. | |
| 6,562,447 B2 | 5/2003 | Leon et al. | |
| 2002/0076554 A1 | 6/2002 | Stopper | |

FOREIGN PATENT DOCUMENTS

| | | |
|---|---|---|
| BR | 9900032 A | 8/2000 |
| DE | 20017205 U1 | 2/2001 |
| EP | 1032366 B1 | 2/2003 |
| FR | 2653059 B1 | 8/1992 |
| WO | WO 01/08640 A | 2/2001 |
| WO | WO 02/085965 A1 | 10/2002 |

* cited by examiner

*Primary Examiner*—Sharon E. Kennedy
(74) *Attorney, Agent, or Firm*—Bridget Murray; Cynthia L. Clay

(57) ABSTRACT

The present invention is directed to a disposable article that contains a plurality of substrate layers. The article is selected from the group consisting of pad sized articles, grip sized articles, sheet sized articles and combinations. These articles have a cleansing composition associated with the substrate layers. The articles provide effective cleansing benefits to the skin and hair in a convenient, inexpensive, and sanitary manner. The articles of the present invention also have superior thickness. Additionally, the article has increased rigidity while at the same time is flexible. The increase in rigidity and thickness provides for an article that does not crush or crumple during use. The article of the present invention can also provide a therapeutic or aesthetic benefit without the need for a separate benefit providing product.

16 Claims, No Drawings

CLEANSING ARTICLE WITH IMPROVED HANDLEABILITY

CROSS REFERENCE TO RELATED APPLICATION(S)

This application claims the benefit of U.S. Provisional Application No. 60/478,631, filed Jun. 13, 2003.

FIELD OF THE INVENTION

The present invention relates to disposable, lathering cleansing articles useful for cleansing the skin, hair, other keratinous surfaces, cleansing dishes and other hard surfaces in need of cleansing. These articles of the present invention are generally planar and preferably have rigidity and thickness values in prescribed ranges, depending on the size of the article which results in improved handleability. These articles comprise a plurality of substrate layers and a cleansing composition associated with the layers which comprises a surfactant.

BACKGROUND OF THE INVENTION

Personal care products, particularly cleansing products, have traditionally been marketed in a variety of forms such as bar soaps, creams, liquid soaps, lotions, and gels. Typically, these cleansing products have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and should not leave the skin or hair with a heavy buildup or overly dry when used frequently.

It is desirable for a planar cleansing article to have rigidity and thickness within a certain range depending on the size of the article. Hand-held articles haven fallen into three categories. A first is articles that have the size of a pad which fits within the palm of a hand. An article in this category, such as a bar of soap and a sanding block must be rigid enough to be pushed (i.e., sideways compression vector) without buckling, and yet compliant enough to follow contours of the underlying plane. A second is grip sized articles, such many existing body sheets for example disclosed in U.S. Pat. Nos. 6,428,799, 6,217,889 and 6,267,975, which are used by gripping a side and pulling (i.e., sideways tension vector). An article in this category must have sufficient rigidity to remain flat during use. A third is sheet sized articles, such as existing washcloths and paper towels. An article in this category must have a low enough rigidity so that they become entwined among the gripping members of the hand (i.e., fingers) during use.

A problem exists with the prior art lathering, cleansing articles in that they are insufficiently rigid to efficiently cleanse the body or other surface without buckling, dragging, crumpling or rolling up or they are so rigid they do not follow contours of the skin or surface being cleansed, they do not retain their shape, and so are ineffective at cleaning. Some articles which are too rigid can be perceived as scratchy or damaging to the skin, and these overly rigid articles do not lather well because their rigidity reduces the ability of successive compression-decompression cycles to pump lather through the article. These articles are unable to cleanse and exfoliate at optimal levels for the user.

It is further desirable for cleansing articles that are personal care articles to be non-scratchy. Articles comprising thermoplastic materials, which are rigid can have a scratchy feel during use, particularly at edges, protrusions and bond points. High Density Polyethylene (HDPE) sheets, for example, at a thickness of only 0.010 inches (0.25 mm), feel scratchy at the edges when articles containing said sheets are rubbed against the skin.

It is also highly desirable to deliver cleansing benefits from a disposable product. Disposable products are convenient because they obviate the need to carry or store cumbersome bottles, bars, jars, tubes, and other forms of clutter including cleansing products and other products capable of providing therapeutic or aesthetic benefits. Disposable products are also a more sanitary alternative to the use of a sponge, washcloth, or other cleansing implement intended for extensive reuse, because such implements can develop bacterial growth, unpleasant odors, and other undesirable characteristics related to repeated use.

Thus, a need exists for an article of varying sizes that have increased handleability. These articles would need a cleansing composition associated with an article that is disposable having a non-scouring substrate with various textures, increased thickness and rigidity. These properties enhance lathering which in turn increases cleansing and exfoliation, and optimizes delivery and deposition of a therapeutic or aesthetic benefit agent, which might be contained within the article.

SUMMARY OF THE INVENTION

The inventors have discovered that the articles of the present invention that are Pad sized article from about 55 $cm^2$ to about 135 $cm^2$ have a rigidity in the Cross Machine Direction (CD) from 0.2 to about 55 gm/cm/cm, a rigidity in the Machine Direction (MD) direction from about 1.0 to about 55 gm/cm/cm and a Low Pressure Thickness from about 2.5 to about 31 mm. Grip sized articles between 136 and and 230 $cm^2$ in size have a rigidity in the Cross Machine Direction (CD) from 0.3 to about 30 gm/cm/cm, a rigidity in the Machine Direction (MD) direction from about 1.6 to about 50 gm/cm/cm and a Low Pressure Thickness from about 1.1 to about 30 mm. Sheet sized articles between 231 and and 500 $cm^2$ in size have a rigidity in the Cross Machine Direction (CD) from 0.15 to about 10 gm/cm/cm, a rigidity in the Machine Direction (MD) direction from about 0.18 to about 30 gm/cm/cm and a Low Pressure Thickness from about 0.40 to about 10 mm. Surprisingly the articles have improved handleability that provides effective cleansing benefits to the skin and hair in a convenient, inexpensive, and sanitary manner while at the same time maintain its softness and flexibility. The increase in rigidity and thickness provides for articles that do not crush or crumple during use. The articles are non-scouring or non-damaging to the skin or surface being cleaned. The cleansing articles of the present invention comprise a plurality of substrate layers and have a cleansing composition associated with the substrate layers. The article of the present invention can also provide a therapeutic or aesthetic benefit without the need for a separate benefit providing product.

In preferred embodiments of the present invention, the article is suitable for personal care applications and is useful for cleansing the skin, hair, and similar keratinous surfaces in need of cleansing. Consumers use this article by wetting it with water and rubbing it on the area to be cleansed.

Although the preferable embodiments of the article of the present invention are for personal care applications, it may also be useful in a variety of other industries including household care, dish care, automotive care, marine vehicle care, and animal care; anywhere surfaces or areas needs cleansing and/or application of a benefit agent; e.g., wax, conditioner, UV protectant, etc.

DETAILED DESCRIPTION OF THE INVENTION

By "composition associated with the article" or "composition associated with the substrate layer(s)" as used herein, means compositions that are applied to or inside of the individual fibers prior to forming the article, permeated into the article, coated onto, within or adjacent to the exposed surfaces of the article. This can include placing the composition into the extruder for the foam layer.

The term "disposable" is used herein in its ordinary sense to mean an article that is disposed or discarded after a limited number of usage events, preferably less than 5, more preferably less than about 3, and even more preferably about 1 entire usage events.

By "fluid" as used herein, means, organic and inorganic compounds and mixtures having a viscosity so that they flow under their own weight and conform to the shape of containers rather than having their own shape. Most fluids have a viscosity of less than about 1,000,000 cP, especially useful fluids for the current invention have a viscosity less than about 100,000 cP, and more useful fluids for the current invention have a viscosity of less than about 10,000 cP as measured by commonly available rheometer and viscometer apparati at temperatures and shear rates relevant to use of said articles. Common fluids for use in or with the current invention include water, mono- and polyhydric alcohols (glycerin, propylene glycol, ethanol, isopropanol, etc.), hydrocarbon oils such as mineral oil, linear and branched esters of hydrocarbons, silicone fluids, and can contain other components dissolved or dispersed within them, or in addition to them.

By a "lathering surfactant" is meant a surfactant, which when combined with a fluid and mechanically agitated generates a foam or lather.

The term "water-activated," as used herein, means that some of the articles of the present invention are presented to the consumer in a form to be used when wetted with a fluid. It is found that these articles produce a lather or are "activated" by either contacting them with a fluid or producing them with a fluid and then further subjecting the article to mechanical forces, such as rubbing.

The term "substantially dry," as used herein, means that prior to use the article is substantially free of fluid and generally feels dry to the touch. As used herein, "substantially dry" means that the articles of the present invention exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms. The determination of the Moisture Retention is discussed later. Thus, the "substantially dry" articles of the present invention will generally comprise less than about 20% by weight of fluid, preferably from 4% to about 20% by weight of fluid, and more preferably from about 4% to about 16% by weight of fluid.

The term "moist," as used herein, means that prior to use the article can feel relatively dry to the touch and still contain high fluid content. Thus, the "moist" articles of the present invention will generally comprise from about 20% to about 40% by weight of fluid.

The term "wet" means that prior to use the article can feel wet to the touch and contain high fluid content. The weight percent of liquid in the "wet" article is based on the total weight of the composition. The weight is expressed as a weight of the total composition. Thus, the "wet" articles of the present invention will generally comprise from about greater than 40% by weight of fluid, preferably from 40% to about 95% by weight of fluid, and more preferably from about 50% to about 80% by weight of fluid.

All percentages and ratios used herein are by weight of the total composition and all measurements made are at 25° C., unless otherwise designated.

Rigidity of Substrate Layer

Preferred substrate materials are those that are sufficiently rigid and have preferred thickness, both properties contribute to improved handleability of articles.

It is desirable to be able to move the articles over surfaces during use without the articles buckling or rolling up during use, i.e., bending. The ability of an article to remain flat and resist bending can be measured by an engineering test known as Three Point Bending (e.g., as described in ASTM Standard D 790-99, "Flexural Properties of Unreinforced and Reinforced Plastics and Electrical Insulating Materials"). Other nonwoven tests, such as the Handle-O-Meter Test (Thwing-Albert Instrument Company, Philadelphia, Pa.) rely on the basic principle of resistance to bending, as measured in 3-point bending mode. An advantage to measuring Three Point Bending instead of the Handle-O-Meter Test is that Three Point Bending can be measured in any web direction, determining properties in the machine direction separately from the cross machine direction. Properties in these two directions are often different for machine made articles, and result in variations in use of the articles which cannot be explained by the simpler measurements. Three Point Bending of materials produces data relating the stress-strain properties of the materials. Because it is common to test materials of differing length, thickness and width, equations are used to reduce data to common units for comparison. For Three Point Bending, Equation 1 can be used, and can be combined with Equation 2 for a rectangular strip of material, which can be a foam, a foam composite, layers comprising foam, or an article.

$$E = \frac{(F)(L)^3}{(v)(6)(I)} \qquad \text{Equation 1}$$

$F$ = force
$L$ = length of sample
$I$ = moment of inertia of sample
$v$ = displacement
$E$ = elastic modulus of material $$I = \frac{(b)(h)^3}{12} \qquad \text{Equation 2}$$

$b$ = width of sample
$h$ = thickness of sample

It can be seen from Equation 1 that the expression $(F/((b)(v))$ is an important component of the rigidity of a nonwoven article as it relates to its ability to resist bending, and $(F/((b)(v))$ is directly available from Three Point Bending testing as the slope in Three Point Bending, divided by the width of the sample tested. Inventors have found that when this slope is within a certain ranges, cleansing articles resist bending during use without becoming too rigid for comfortability, making the articles easier to handle. Further, it can be seen from the combination of Equation 1 and Equation 2, expressed below as Equation 3 (rearranged), that thickness of articles (h) is also an integral component of its rigidity or (F/((b)(v)), the expressed rigidity scaling as a cubic function of thickness.

$$\frac{F}{((b)(v))} = \frac{(E)(h)^3}{(2)(L)^3}$$ Equation 3

Three Point Bending Rigidity Method

Three Point Bending Rigidity is tested on a Texture Analyzer model TA-xt2i (Texture Technologies, Scarsdale, N.Y., USA) using a 5 kg load cell, a three point bending geometry, and samples (web materials or articles) having widths and lengths of about 3.0 inches and 5.5 inches. First, a lower stage is established for the test, consisting of two parallel beams each having a diameter (o.d.) of 1.05 inches. Schedule 40 pipe having a ¾ in. i.d. is widely available, easy to use, and may be suitable for fabricating the lower stage. The lower stage is prepared so that the beams are fixed in a parallel position having a gap between them measuring 1.85 inches at the narrowest point (i.e., a center-to-center distance of 2.90 inches). The length of the beams is sufficiently long that a sample (a web or an article) may be balanced on the beams and be fully supported by the beams with the substrate clear of any support structures used to fix the beams in position. A length of 10 inches is effective for the beams. The lower stage is set in place at the base of the Texture Analyzer in a position high enough that an upper beam can penetrate through the space between the parallel beams of the lower stage during a measurement.

An upper stage is prepared, which comprises a T-shaped upper beam, having a measurement section and a bisecting section. The measurement section of the T-shaped upper beam is the middle beam as conventionally described in Three Point Bending literature, and the bisecting section is used to affix the T-shaped upper beam to the Texture Analyzer TA-xt2i. The upper beam has an outer diameter measuring 1.305 inches and a length measuring 3.10 inches, measuring the central measurement section of the beam. The upper stage is affixed to the upper movable arm of the Texture Analyzer TA-xt2i in a position so that the measurement section (i.e., the middle beam of the Three Point Bending geometry) of the upper beam is parallel to the two parallel beams of the lower stage, all of which are positioned horizontally. The stages are fixed in position so that as the upper beam is lowered by the Texture Analyzer TA-xt2i, the upper beam advances vertically (downward) so that the measurement section intersects the plane of the lower stage midway between the parallel beams of the lower stage; and the advancement of the upper beam movement is in a direction perpendicular to the plane formed by the parallel beams of the lower stage. The upper beam is set at a starting position, which is a height where the lowest portion of the upper beam is 1.25 inches above the highest portion of the parallel beams on the lower stage. The instrument is calibrated properly and set to measure at an upper beam (i.e., Texture Analyzer TA-xt2i upper arm speed) velocity of 10 mm per second in a downward direction, measuring the force in compression. The instrument is programmed to travel a distance of 60 mm, collect force and displacement data (100 points per second minimum) and return to the starting position.

Web and article are used interchangeably to mean both in the following, and a strip can be of either. Three Point Bending Rigidity is measured for webs and articles from which lathering surfactant composition has been substantially removed. Articles are flushed with water to remove chemical component while keeping the article flat. The article is then laid flat and blotted dry on cellulose paper towels until the water content no longer interferes with measurement of the bending modulus (for example by causing frictional drag on the lower beams, or by carrying excessive weight). Generally, articles should be measured at less than 100% water content, by weight of the substrate. Preferably, the articles should be air dried to below about 25% water content. If the chemical component does not contribute substantially to the bending modulus, the articles can be measured without removal of the chemicals as is, if they are essentially dry, or blotted dry if they are not. A first sample is prepared by cutting a web or article into a strip measuring 3 inches wide and 5.5 inches long with the long dimension (5.5 inches) in the MD; a second sample is prepared by cutting a web or article into a strip with the long dimension (5.5 inches) in the CD. If preparing an article delaminates it, the ends of the article or strips are taped to maintain integrity. If articles are less than 3 inches wide, they are not cut but are run as is. If articles are sealed near an edge (within 5 mm), then at least some strips cut should include the sealed edge portion of the article. If an MD and a CD of an article are not clearly established for any reason, the direction of maximum rigidity is selected to be the MD and the CD is selected to be orthogonal to the MD. If a width of 3 inches is unattainable in either direction due to size of the article, then strips are cut with narrower width than 3 inches and the measurement is performed, the measured width being used later to normalize the data by width. If an article has a length or width between 3.0 inches and 5.5 inches, shorter lengths are cut, so long as the article can be cut to long dimensions of at least 3 inches, and are used with the stages as described. If the article can only be cut to long dimensions less than 3 inches, an alternate lower stage is prepared which is a rigid, flat surface having a long 2-inch wide slot cut through it, and is used as the lower stage by setting it in position such that the long sides of the slot are parallel to the upper beam such that a Three-Point Bending geometry is attained for articles having long dimensions as small as 2 inches. For these short articles measured with the alternate stage, the slopes obtained as described below are multiplied by the factor 0.328 to obtain the rigidity, said factor normalizing them to a consistent length, being equal to the cube of the ratio of the 2 inch stage length to the 2.9 inch stage length. If articles have unusual shapes (oval, sphere, wishbone, e.g.) and are smaller than 3 inches in width, they can be measured without cutting strips using the alternate lower stage, and the width across the center, where stress is the greatest, is used as the width of the sample in cm as described below. If the articles become hard when dried such as occurs due to hydrogen bonding such as for cellulosic sponges or cellulose or rayon containing nonwovens, the articles should be run slightly damp, containing about 25% water by weight of the dry substrate, which condition represents the article properties at the end of the use cycle. If the articles have a rigidity that increases substantially during the use cycle, such as for example the effervescent pillow articles disclosed herein, the articles are measured at the point during their use of maximum rigidity, for example as they are wet and without cutting strips, instead measuring length and width and normalizing the resulting data accordingly.

Rigidity in the Machine Direction (MD) is measured. A first strip is placed flat across the lower stage beams with the long dimension traversing the gap between the lower beams, being careful not to bend the strip during preparation, the major axis of the strip orthogonal to the axis of the lower beams, and is centered on the beams in a position immediately below the upper beam. The upper beam advances at a rate of 10 mm/sec downward, at first contacting and then bending the strip, collecting force-displacement information. The results are plotted as force (F, y-axis in grams) and displacement (v, X-axis in centimeters). Displacement is plotted as its absolute value so that it is increasing and positive with downward movement with the upper beam. The rigidity is determined from a graph of the results. The results have a first portion where F is equal to zero (prior to contact); a second portion where F is greater than zero and increasing non-linearly (i.e., curving upwards on the graph) due to a sum of preliminary forces on the article (compression and bending, e.g.); and a third portion where a primary force component is the force necessary to bend the article. Results in the third portion are used to evaluate the rigidity. At least a fourth portion of the results is often visible, where the force begins to plateau, and may level out and remain flat or level out and increase due to compression of thick samples between the side beams and center beam, which results are not used. A linear portion of the results is selected within the third portion of the results, after the end of the curved second portion and prior to the onset of the fourth portion of the results, and the slope of the graph is determined by regression, which is F/v and is expressed in grams/cm. The linear portion of the results selected is broad enough that the results are not overly influenced by noise or jaggedness of the results, so that the results are representative of the trend, usually about 0.2 to 0.6 cm in width. If a linear portion is not apparent, a region is selected by choosing the data range between one sixth and one half the highest force obtained for the measurement as the range for regression of the slope. The resulting slope is divided by the width of the sample in cm (usually 7.62 cm) to obtain the MD Rigidity, in grams/cm/cm, which normalizes the rigidity by width. A sufficient number of samples are measured to obtain a representative average, alternating the side of the sample facing upwards for each subsequent measurement. Second strips, having long dimensions in the CD, are measured and results evaluated in the same manner to obtain the Rigidity in the Cross Machine Direction (CD).

Substrate Layer

The articles of the present invention comprise a plurality of substrate layers. The term "layer" as used herein means a water insoluble domain which may exist as a prior web and which is a structural component of an article, providing a primary contribution to the structural integrity of said article, such as rigidity, strength, toughness, thickness, loft, etc. A layer can include discontinuous domains such as formed by a composite, the layer need not having existed as a prior web nor having a continuous X-Y orientation in order to be a layer. The term "plurality," as used herein, means that the article as described in the present invention comprises at least two substrate layers regardless of whether the layers (existed as a prior web or webs) and are formed individually and then combined or co-formed such as a composite. The term laminate means at least one layer existed apart from the article and is combined to form an article by a lamination process, including thermal (including ultrasonic) and adhesive bonding lamination processes. The term composite means that at least one layer did not exist as a distinct layer apart from the article, said layer being formed during a processing step involving mixing of two or more components or compositions to form a heterogeneous mixture. Preferably, the substrate is soft yet invigorating to the skin of the consumer when used exhibits a pillow-like loftiness. Each layer has both an interior and exterior surface. In both cases, the interior surfaces of the layers are those which face the inside or innermost portion of the article of the present invention whereas the exterior surfaces of the layers are those which face the outside or outermost portion of the article. The term "substrate" as used herein, means an article comprising a plurality of layers wherein each layer is selected from the group consisting of nonwovens, wovens, foams, films, formed films, scrims and combinations thereof.

Without being limited by theory, the substrate enhances cleansing. The substrate can have the same or differing textures on each side. The substrate may act as an efficient lathering and exfoliating implement. By physically coming into contact with the skin or hair, the substrate significantly aids in cleansing and removal of dirt, makeup, dead skin, and other debris. In preferred personal care embodiments, however, the substrate is non-scouring or nonabrasive to the skin.

These articles of the present invention are generally planar and preferably have rigidity and thickness values in prescribed ranges, depending on the size of the article. Pad articles come in sizes from about 55 $cm^2$ to about 135 $cm^2$ in size. The Pad sized articles have a rigidity in the Cross Machine Direction (CD) from 0.2 gm/cm/cm to about 55 gm/cm/cm, preferably from 0.4 gm/cm/cm to about 20 gm/cm/cm, more preferably from about 0.5 gm/cm/cm to about 11 gm/cm/cm, even more preferably from about 0.5 gm/cm/cm to about 8 gm/cm/cm, and still even more preferably from about 0.5 gm/cm/cm to about 5 gm/cm/cm, as measured by the Three Point Bending Rigidity Method described herein. The Pad sized article has a rigidity in the Machine Direction (MD) direction from about 1.0 gm/cm/cm to about 55 gm/cm/cm, preferably from about 1 gm/cm/cm to about 20 gm/cm/cm, more preferably from about 1 gm/cm/cm to 11 gm/cm/cm, even more preferably from about 1.6 gm/cm/cm to about 8 gm/cm/cm, still even more preferably from about 1.8 gm/cm/cm to about 6 gm/cm/cm, as measured by the Three Point Bending Rigidity Method described herein. The Pad sized article has a Low Pressure Thickness from about 2.5 mm to about 31 mm, preferably from 2 mm to about 25 mm, more preferably from about 2 mm to about 10 mm, even more preferably from about 2 mm to about 15 mm, still more preferably from about 1.8 mm to about 12, and still even more preferably from about 1.8 mm to about 9 mm.

Grip sized articles between 136 to about 230 $cm^2$ in size have a rigidity in the Cross Machine Direction (CD) from 0.3 gm/cm/cm to about 30 gm/cm/cm, preferably from 0.4 gm/cm/cm to about 20 gm/cm/cm, more preferably from about 0.5 gm/cm/cm to about 15 gm/cm/cm, even more preferably from about 0.5 gm/cm/cm to about 10 gm/cm/cm, as measured by the Three Point Bending Rigidity Method described herein. The Grip sized article has a rigidity in the Machine Direction (MD) direction from about 1.6 gm/cm/cm to about 50 gm/cm/cm, preferably from about 1.7 gm/cm/cm to about 30 gm/cm/cm, more preferably from about 1.8 gm/cm/cm to about 25 gm/cm/cm, even more preferably from about 1.5 gm/cm/cm to about 20 gm/cm/cm, as measured by the Three Point Bending Rigidity Method described herein. The Grip sized article has a Low Pressure Thickness from about 1.1 mm to about 30 mm, preferably from 1.2 mm to about 27 mm, more preferably from about 1.3 mm to about 25 mm, even more preferably from about 1.5 mm to about 20 mm.

Sheet sized articles between 231 to about 500 cm² in size have a rigidity in the Cross Machine Direction (CD) from 0.15 gm/cm/cm to about 10 gm/cm/cm, preferably from 0.16 gm/cm/cm to about 8 gm/cm/cm, more preferably from about 0.17 gm/cm/cm to about 5 gm/cm/cm, even more preferably from about 0.2 gm/cm/cm to about 4 gm/cm/cm, and still even more preferably from about 0.25 gm/cm/cm to about 4 gm/cm/cm, as measured by the Three Point Bending Rigidity Method described herein. The Sheet sized article has a rigidity in the Machine Direction (MD) direction from about 0.18 gm/cm/cm to about 30 gm/cm/cm, preferably from about 0.2 gm/cm/cm to about 20 gm/cm/cm, more preferably from about 0.25 gm/cm/cm to about 10 gm/cm/cm, even more preferably from about 0.3 gm/cm/cm to about 8 gm/cm/cm, and still even more preferably from about 0.4 gm/cm/cm to about 6 gm/cm/cm, as measured by the Three Point Bending Rigidity Method described herein. The Sheet sized article has a Low Pressure Thickness from about 0.40 mm to about 10 mm, preferably from 0.6 mm to about 5 mm, more preferably from about 0.75 mm to about 4 mm, even more preferably from about 0.8 mm to about 3 mm, and still even more preferably from about 0.9 to about 2 mm.

The substrate layer may comprise a variety of both natural and synthetic fibers or materials. As used herein, "natural" means that the materials are derived from plants, animals, insects or byproducts of plants, animals, and insects. The conventional base starting material is usually a fibrous web comprising any of the common synthetic or natural textile-length fibers, or combinations thereof.

Nonlimiting examples of natural materials useful in the present invention include, but are not limited to, silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and combinations thereof. Cellulosic fiber materials are preferred in the present invention.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, formed films, films, foams, extruded foams, pillows, effervescent pillows and combinations thereof. Examples of suitable synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, polybutylene terephthalate fiber, dacron; polyolefins such as polypropylene, polyethylene; polyvinyl acetate fibers; polyurethane foams and combinations thereof. These and other suitable fibers and the nonwovens prepared there from are generally described in Riedel, "Nonwoven Bonding Methods and Materials," *Nonwoven World* (1987); *The Encyclopedia Americana*, vol. 11, pp. 147-153, and vol. 26, pp. 566-581 (1984); U.S. Pat. No. 4,891,227, to Thaman et al., issued Jan. 2, 1990; and U.S. Pat. No. 4,891,228. As used herein, "nonwoven" means that the layer comprises fibers which are not woven into a fabric but rather are formed into a sheet, mat, or pad layer. The fibers can either be random (i.e., randomly aligned) or they can be carded (i.e., combed to be oriented in primarily one direction). Nonwoven substrates made from synthetic materials useful in the present invention can be obtained from a wide variety of commercial sources.

More preferred synthetic fibers for the substrate layer are solid staple polyester fibers, which comprise polyethylene terephthalate homopolymers. Suitable synthetic materials may include solid single component and multicomponent synthetic fibers, i.e., more than one type of material making up the fibers. The synthetic fibers may comprise bicomponent or dual component fibers. Such bicomponent fibers may have a core and a sheath configuration or a side-by-side configuration. In either instance, the substrate layer may comprise either a combination of fibers comprising the above-listed materials or fibers which themselves comprise a combination of the above-listed materials.

For the core-sheath fibers, preferably, the cores comprise materials selected from the group consisting of polyesters, polyolefins having a $T_g$ or melting point of at least about 10° C. higher than the sheath material, and combinations thereof. Conversely, the sheaths of the bicomponent fibers preferably comprise materials selected from the group consisting of polyolefins having a $T_g$ or melting point of at least about 10° C. lower than the core material, and polyesters having a $T_g$ or melting point of at least about 10° C. lower than the core material, and combinations thereof.

In any instance, side-by side configuration or core-sheath configuration, the fibers of the substrate layer may exhibit a helical or spiral configuration, particularly the bicomponent type fibers.

A preferred synthetic material for a scouring substrate layer may comprise nylon fibers. A more preferred synthetic material comprises nylon fibers formed into a scrim layer having additional nylon fibers bonded thereto such that the additional fibers form arcs on the scrim layer.

Natural material nonwovens useful in the present invention may be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Additional suitable nonwoven materials include, but are not limited to, those disclosed in U.S. Pat. No. 4,447,294, issued to Osborn on May 8, 1984; U.S. Pat. No. 4,603,176 issued to Bjorkquist on Jul. 29, 1986; U.S. Pat. No. 4,981,557 issued to Bjorkquist on Jan. 1, 1991; U.S. Pat. No. 5,085,736 issued to Bjorkqui on Feb. 4, 1992; U.S. Pat. No. 5,138,002 issued to Bjorkquist on Aug. 8, 1992; U.S. Pat. No. 5,262,007 issued to Phan et al. on Nov. 16, 1993; U.S. Pat. No. 5,264,082, issued to Phan et al. on Nov. 23, 1993; U.S. Pat. No. 4,637,859 issued to Trokhan on Jan. 20, 1987; U.S. Pat. No. 4,529,480 issued to Trokhan on Jul. 16, 1985; U.S. Pat. No. 4,687,153 issued to McNeil on Aug. 18, 1987; U.S. Pat. No. 5,223,096 issued to Phan et al. on Jun. 29, 1993 and U.S. Pat. No. 5,679,222, issued to Rasch et al. on Oct. 21, 1997.

Additional suitable materials include but are not limited to, formed films and composite materials, i.e., multiply materials containing formed films. Preferably, such formed films comprise plastics which tend to be soft to the skin. Suitable soft plastic formed films include, but are not limited to, polyolefins such as low density polyethylenes (LDPE). In a preferred embodiment of the present invention the lathering cleansing article comprises a foam layer. Inventors have found certain foam materials are beneficial in multiple layer articles due to their ability to affect a bond at a bond point between adjacent nonwovens, by melting and resolidifying. Additionally, the foam layer can be beneficial in multiple layers where they do not affect a bond between nonwoven layers. In this embodiment the foam layer is non-bonded.

The foam layer can be in the form of a composite where the foam layer partially or fully penetrates another layer, or where another layer partially or fully penetrates the foam so that it is found within or around the other substrate layers described herein. Neither the foam layer nor the other substrate layers need to have existed as prior layers in a composite comprising the foam. Nonlimiting examples of composites comprising the foam layer include a second nonwoven web or formed film joined to the foam layer precursor layer which is a molten or semi-molten sheet at the extruder outlet such that a heterogeneous or homogenous (in the case of construction of both foam and web of the same polymer) transition zone exists between the foam and second web; and a layer of carded, spunbond or meltblown fibers added to a foam web either by an adhesive joining process or when either the foam web or the fibers is in a molten or semi-molten state such that a homogeneous or heterogeneous composite or composite zone is formed between the layers. The other layers include fibrous nonwovens comprising natural and synthetic fibers and blends of natural and synthetic fibers including meltblown, spunbond, hydroentagled, airlaid, multicomponent and multiconstituent fiber and/or fibrous webs, other foams including coextruded layers or domains one within the other, films including formed films that have apertures or openings and scrims, and/or co-processed with other webs such as selective mechanical deformation as described in U.S. application Ser. No. 10/737,640 filed on Dec. 16, 2003. When a composite is formed the foam layer can maintain its own foam domain within the composite.

The foam layer has a distinct basis weight. When the foam exists or existed as a separate layer, the basis weight of the foam is the same as the basis weight of the preexisting foam layer. When the foam is combined with other chemical or non-chemical components, the foam can have a lower basis weight as a result of the ability of the other components to extend the foam. The basis weight of the foam as a separate layer is from about 1 gsm to about 250 gsm, preferably from about 3 gsm to about 200 gsm, more preferably from about 5 gsm to about 150 gsm, even more preferably from about 7.5 gsm to about 100 gsm, still even more preferably from about 10 gsm to about 80 gsm. The basis weight of the foam when it comprises other chemical and non-chemical components is from about 0.5 gsm to about 250 gsm, preferably from about 3 gsm to about 200 gsm, more preferably from about 5 gsm to about 150 gsm, even more preferably from about 7.5 gsm to about 100 gsm, still even more preferably from about 10 gsm to about 80 gsm.

The foam layer provides superior thickness, rigidity and softness to the articles of the present invention. The increase in thickness and rigidity enhances lathering, which in turn increases cleansing and exfoliation. Additionally, the foam layer prevents the article from being crushed or crumpled during use but still provides for a soft flexible article.

When the foam layer is a composite, the properties of the foam layer can be determined by physical separation of the foam layer from the attached layer wherein a transition, composite zone between the foam layer and attached layer can be included or not included; or the foam composite can be the foam layer, inclusive of the second layer or material, and the properties of the composite are the properties of the foam layer. Preferably the foam layer of the present invention is permeable. Slitting or punching the extruded foam layer can accomplish this if the foam layer is a closed cell foam, or to increase permeability if the foam layer is an open cell foam. Preferably, the foam layer is a closed cell foam which is permeable.

The foam layer has two surfaces, a top surface and a bottom surface. The surfaces of the foam layer can have the same or differing textures on the top and bottom surface. Nonlimiting examples of differing textures can include protrusions, projections, partially heating areas of the surface of the foam to form nodules, nodes, bumps, ridges, creped structures on one or both surfaces of the foam layer. When areas of the foam are melted, the density of the foam area or domain that has not been melted is defined as the foam domain.

When using thermoplastic materials, the density of thermoplastic materials is reduced by preparing the sheets as a foam having a reduced density, which reduces scratchiness. Inventors have found foams for use in articles described herein have preferred density ranges contributing to both improved handleability and reduced scratchy or non-scouring feel against the skin. Articles of the present invention useful for cleansing and/or conditioning the skin are preferably non-scouring. As used herein, "non-scouring" means having an Abrasiveness Value of greater than about 15, preferably greater than about 30, more preferably great than about 50, even more preferably greater than about 70, and most preferably greater than about 80, as defined by the Abrasiveness Value Methodology described below. The extruded foam layer of the present invention has a Density from 0.0001 gm/cm$^3$ to about 0.25 gm/cm$^3$, preferably at least 0.0001 gm/cm$^3$ to about 0.2 gm/cm$^3$, more preferably from about 0.0001 gm/cm$^3$ to about 0.15 gm/cm$^3$, even more preferably from about 0.0001 gm/cm$^3$ to about 0.1 gm/cm$^3$, still more preferably from about 0.005 gm/cm$^3$ to about 0.075 gm/cm$^3$, even still more preferably from about 0.01 gm/cm$^3$ to about 0.032 gm/cm$^3$, yet even still more preferably 0.0001 gm/cm$^3$ as defined by the Calculated Density Method or the Immersion Density Method described below.

The extruded foam layer can be prepared using a blowing agent. The blowing agent may be of the type well known and widely used for the production of expanded polystyrene and polyolefins including polypropylene. Nonlimiting examples of organic blowing agents include, but are not limited to azodicarbonamide, diazoaminobenzene, azo-bis-isobutyronitrile and analogs thereof; and chemical blowing agents such as, ammonium carbonate, sodium bicarbonate and the like. Physical blowing agents such as nitrogen, carbon dioxide and other inert gases and agents that undergo phase change from liquid to gas during the foaming process such as chlorofluorocarbons (CFC), HCFC, low boiling alcohols, ketones and hydrocarbons, are also known for these uses and may also be found useful in the practice of this invention. The blowing agent may further comprise one or more additives to reduce its decomposition temperature The foam layer of the present invention is in the form of open cell, closed cell, double cell, reticulated foams, loaded foams, multiple layer foams and combinations thereof. Preferably, the foam layer is a closed cell foam. Additionally, the foam layer can be extruded as a rope lattice, sheets or in strands.

Nonlimiting examples of foam materials useful in the present invention include, but are not limited to polyethylene foams, polypropylene foams, vinyl foams, acrylic foams, polyether foams, polyester foams, polyurethane foams, foam comprising blends of miscible and immiscible polymers and copolymers, silicone sponge foam, neoprene foams, rubber foams, polyolefin foams and mixtures thereof.

Preferably, the foam material is high density polyethylene (HDPE) and high density polypropylene (PP).

In the present invention, various kinds of additives can be mixed into the foam layer as necessary such as anti-shrinking agents, foam regulators, lubricants, colorants, thermal stabilizers, anti-oxidants, crystallization nucleateing agents, inorganic fillers, and rubbers.

Methods of making nonwovens are well known in the art. Generally, these nonwovens can be made by air-laying, water-laying, meltblowing, coforming, spunbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including, but not limited to, meltblowing, spunbonding, air-entanglement, hydroentanglement, thermal bonding, selective mechanical deformation as described in U.S. application Ser. No. 10/737,640 filed on Dec. 16, 2003, and combinations of these processes.

Cleansing Compositions

The present invention comprises articles which have cleansing compositions associated with them. The articles are preferably substantially dry, but they can be substantially dry, moist or wet. Preferably these articles are personal care articles with a personal care composition used by individuals primarily for cleansing and, or treatment of skin, hair or other and similar keratin-containing surfaces including skin, hair and finger and toe nails. The surfactants of the cleansing composition may be lathering or non-lathering surfactants. Preferably, the articles of the present invention comprise one or more lathering surfactants that are associated with the article of the present invention. Thus the lathering or non-lathering surfactants can be associated with the article. Generally this will be done prior to the point of use of the article, i.e., the surfactants will be combined with the article before the article is ultimately wetted for use.

In an embodiment of the present invention, cleansing articles can be used by individuals for dish washing. The hard surface compositions used in dishwashing will preferably comprise a cleansing paste preferably comprising a surfactant. By 'paste' is meant herein that the material is in a solid state and does not continuously change its shape or yield when subjected to a given stress preferably of about 50 to about 160 Pa at 25° C.

In the context of this application, lathering surfactant means a surfactant, that when combined with a fluid and mechanically agitated, generates foam or lather sufficient to cause the article that it's associated with to form a lather. Preferably, these lathering surfactants and, or their combination with other surfactants should be mild, which means that these surfactants provide sufficient cleansing or detersive benefits but do not overly dry the skin or hair.

A wide variety of lathering surfactants are useful for the cleansing compositions described herein and include those selected from the group consisting of anionic lathering surfactants, nonionic lather surfactants, amphoteric lathering surfactants, and mixtures thereof. Non-limiting examples of lathering surfactants useful in the compositions of the present invention are disclosed in U.S. Pat. No. 6,280,757, to McAtee et al., issued Aug. 28, 2001. Generally, the lathering surfactants do not strongly interfere with deposition of any conditioning agents that are present, e.g., are fairly water soluble, and usually have an HLB value of above 10. Cationic surfactants can also be used as optional components, provided they do not negatively impact the overall lathering characteristics of the required lathering surfactants.

1) Lathering Personal Care Compositions

The lathering personal care compositions of the present invention an comprise a sufficient amount of one or more lathering surfactants such that the compositions associated with the article are capable of generating from at the least about 1500 ml of Steady Flash Lather Volume according to the Steady Lather Volume Test described below. The lathering personal care composition associated with the article generates from about 2200 ml to about 8000 ml of Steady Total Lather Volume, preferably at the least about 2500 ml of Steady Total Lather Volume, more preferably at least about 3000 ml of Steady Total Lather Volume, even more preferably at least about 4000 ml of Steady Total Lather Volume, still more preferably at least about 5000 ml of Steady Total Lather Volume, and still even more preferably at least about 5500 ml of Steady Total Lather Volume.

Generally a personal care composition will comprise no more than about 1600 weight percent by weight of the substrate of the lathering surfactant, preferably comprise no more than about 1000 weight percent, more preferably no more than about 800 weight percent, and still more preferably no more than about 600 weight percent by weight of the substrate of a lathering surfactant. Generally the cleansing composition will preferably comprise at least 15 weight percent by weight of the substrate of the lathering surfactant, preferably at least 25 weight percent, more preferably at least 50 weight percent, and still more preferably at least 60 weight percent by weight of the substrate of a lathering surfactant. The article will comprise from about 1.1 to about 10 grams of surfactant per article, preferably from about 1.25 grams to about 8 grams of a lathering surfactant per article, more preferably from about 1.3 grams to about 6 grams of a lathering surfactant per article.

Suitable Surfactants for the personal care compositions described above include the following surfactants:

Anionic Lathering Surfactants

Non-limiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic lathering surfactants are useful herein. Non-limiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein include are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-ionic Lathering Surfactants

Non-limiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992);

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Non-limiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

2) Non-Lathering Personal Care Compositions

The non-lathering personal care compositions of the present invention can comprise a sufficient amount of one or more non-lathering surfactants such that the compositions associated with the article are capable of generating from at the most 700 ml of Steady Flash Lather Volume according to the Steady Lather Volume Test described below. Preferably the non-lathering personal care composition generates less than 400 ml of Steady Flash Lather Volume, even more preferably less than 300 ml of Steady Flash Lather Volume, and still even more preferably less than 250 ml of Steady Flash Lather Volume.

Generally the non-lathering personal care composition will preferably comprise no more than about 1600 weight percent by weight of the substrate of the non-lathering surfactant, preferably comprise no more than about 1000 weight percent, more preferably no more than about 800 weight percent, and still more preferably no more than about 600 weight percent by weight of the substrate of a non-lathering surfactant. Generally the non-lathering cleansing composition will preferably comprise at least 15 weight percent by weight of the substrate of the non-lathering surfactant, preferably at least 25 weight percent, more preferably at least 50 weight percent, and still more preferably at least 60 weight percent by weight of the substrate of a non-lathering surfactant.

Non-lathering articles will be used for exfoliation, wiping clothes (e.g., wet wipes, refreshment wipes) where lather is not desirable and to lie on skin. Nonlimiting examples of these are skin wiping compositions and refreshing compositions.

Nonlimiting examples of these non-lathering surfactants are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, PPG-2 methyl glucose ether distearate, ceteth-10, diethanolamine cetyl phosphate, glyceryl stearate, PEG-100 stearate, and mixtures thereof.

Optional Ingredients

The lathering personal care and non-lathering personal compositions of the present invention may contain one or more additional skin care components. In a preferred embodiment, where the compositions are to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention.

In any embodiment of the present invention, however, the additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

Benefit Agents

The articles of the present invention can comprise a benefit agent that is useful for providing a therapeutic benefit and/or cosmetic benefit to the skin, hair and similar keratin-containing surfaces during the use of the article. The benefit agents are suitable for application to keratin-containing tissue, that is, they are suitable for use in contact with human keratin-containing tissue without undue toxicity, incompatibility, instability, allergic response, and the like within the scope of sound medical judgment.

The benefit agent can comprise no more than about 1600 weight percent of a substrate of a benefit agent, preferably no more than about 1000 weight percent, more preferably no more than about 800 weight percent, and most preferably no more than about 600 weight percent of a substrate of a benefit agent. The benefit agent can comprise at least 0.05 weight percent of a substrate of a benefit agent, preferably at least 15 weight percent, more preferably at least 15 weight percent, and most preferably no more than about 60 weight percent of a substrate of a benefit agent.

The benefit agents useful in the present invention can comprise compositions described herein. The optional components useful herein can be categorized by their therapeutic or aesthetic benefit or their postulated mode of action. However, it is to be understood that the optional components useful herein can in some instances provide more than one therapeutic or aesthetic benefit or operate via more than one mode of action. Therefore, classifications herein are made for the sake of convenience and are not intended to limit the component to that particular application or applications listed. Also, when applicable, the pharmaceutically-acceptable salts of the components are useful herein.

The articles of the present invention may optionally contain one or more of such optional ingredients. Examples of these ingredient classes include: enzymes, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, additional antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), humectants, opacifying agents, pH adjusters, propellants, reducing agents, sequestrants, skin bleaching agents (or lightening agents) (e.g., hydroquinone, kojic acid, ascorbic acid, magnesium ascorbyl phosphate, ascorbyl glucosamine), skin-conditioning agents (humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, including agents for preventing, retarding, arresting, and/or reversing skin wrinkles (e.g., alpha-hydroxy acids such as lactic acid and glycolic acid and beta-hydroxy acids such as salicylic acid), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like). The articles of the present invention may include carrier components such as are known in the art. Such carriers can include one or more compatible liquid or solid filler diluents or vehicles which are suitable for application to skin or hair.

The articles of the present invention may optionally contain one or more of such optional components. Preferred articles optionally contain a safe and effective amount of an therapeutic benefit component comprising a therapeutic benefit agent selected from the group consisting of vitamin compounds, conditioning agents, skin treating agents, anti-acne actives, anti-wrinkle actives, anti-skin atrophy actives, anti-inflammatory actives, topical anesthetics, artificial tanning actives and accelerators, anti-microbial actives, anti-fungal actives, sunscreen actives, anti-oxidants, skin exfoliating agents, and combinations thereof. As used herein, "a safe and effective amount" means an amount of a compound or component sufficient to significantly induce a positive effect or benefit, but low enough to avoid serious side effects, (e.g., undue toxicity or allergic reaction), i.e., to provide a reasonable benefit to risk ratio, within the scope of sound medical judgment.

Conditioning Agents

The articles of the present invention can comprise a conditioning agent that is useful for providing a conditioning benefit to the skin, hair and other parts of the body with keratin-containing tissue. The conditioning agent can comprise no more than about 1600 weight percent of a substrate of a conditioning agent, preferably no more than about 1000 weight percent, more preferably no more than about 800 weight percent, and most preferably no more than about 600 weight percent of a substrate of a conditioning agent. The conditioning agent can comprise at least 0.05 weight percent of a substrate of a conditioning agent, preferably at least 15 weight percent, more preferably at least 15 weight percent, and most preferably no more than about 60 weight percent of a substrate of a conditioning agent.

The conditioning agent useful in the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5.

Solubility parameters are well known to the formulation chemist of ordinary skill in the art and are routinely used as a guide for determining compatibilities and solubilities of materials in the formulation process. See "Solubility Effects in Product, Package, Penetration, and Preservation", Cosmetics and Toiletries vol. 103, p 47-69, (October 1988).

Non-limiting examples of useful conditioning agents include those selected from the group consisting of petrolatum, fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters, triglycerides and mixtures thereof.

More particularly, the conditioning agent may be selected from the group consisting of paraffin, mineral oil, petrolatum, stearyl alcohol, cetyl alchohol, cetearyl alcohol, behenyl alcohol, C10-30 polyesters of sucrose, stearic acid, palmitic acid, behenic acid, oleic acid, linoleic acid, myristic acid, lauric acid, ricinoleic acid, steareth-1-100, cetereath 1-100, cholesterols, cholesterol esters, glyceryl tribehenate, glyceryl dipalmitate, glyceryl monostearate, trihydroxystearin, ozokerite wax, jojoba wax, lanolin wax, ethylene glycol disteurate, candelilla wax, carnauba wax, beeswax, and silicone waxes.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415-417 (1993).

Petrolatum, which is also known as petroleum jelly, is a colloidal system comprising nonstraight-chain solid hydrocarbons and high-boiling liquid hydrocarbons. See The Merck Index, Tenth Edition, Entry 7047, p. 1033 (1983); Schindler, Drug. Cosmet. Ind., 89, 36-37, 76, 78-80, 82 (1961); and International Cosmetic Ingredient Dictionary, Fifth Edition, vol. 1, p. 537 (1993).

Nonvolatile silicones such as polydialkylsiloxanes, polydiarylsiloxanes, and polyalkarylsiloxanes are also useful skin conditioning agents. These silicones are disclosed in U.S. Pat. No. 5,069,897, to Orr, issued Dec. 3, 1991.

The conditioning agent preferably used in the present invention may also comprise a conditioning emulsion that is useful for providing a conditioning benefit to the skin, hair and similar keratin-containing surfaces during the use of the article. The term "conditioning emulsion" as used herein can either mean the combination of an internal phase comprising a water soluble conditioning agent that is enveloped by an external phase comprising an oil soluble agent or the term "conditioning emulsion" as used herein means the combination of an internal phase comprising an oil soluble agent that is enveloped by an external phase comprising a water soluble agent. In preferred embodiments, the conditioning emulsion would further comprise an emulsifier. The conditioning emulsion comprises from about 15% to about 1600%, preferably from about 25% to about 1000%, more preferably from about 50% to about 800%, and most preferably from about 60% to about 600% by weight of said water insoluble fibrous, non-woven web. In a preferred embodiment the conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

Cationic Polymers

The present invention may also omprise an organic cationic deposition polymer. Concentrations of the cationic deposition polymer preferably range from about 0.025% to about 3%, more preferably from about 0.05% to about 2%, even more preferably from about 0.1% to about 1%, by weight of the cleansing composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Nonlimiting examples of cationic deposition polymers for use in the personal care composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the personal care composition ranges from about 0.025% to about 5%, preferably from about 0.1% to about 3%, more preferably from about 0.2% to about 1%, by weight of the composition.

A nonlimiting example of a commercially available synthetic cationic polymer for use in the cleansing composition is polymethyacrylamidopropyl trimonium chloride, available under the trade name POLYCARE 133, from Rhodia, Cranberry, N.J., U.S.A.

Cationic Surfactants

Cationic surfactants are typically categorized as non-lathering surfactants but may be used in the articles of the present invention provided they do not negatively impact the desired benefits of the articles.

Nonlimiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of cationic surfactants useful herein include cationic alkyl ammonium salts such as those having the formula:

$$R_1R_2R_3R_4N^+X^-$$

wherein $R_1$, is selected from an alkyl group having from about 12 to about 18 carbon atoms, or aromatic, aryl or alkaryl groups having from about 12 to about 18 carbon atoms; $R_2$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO$—$(CH_2)_n$—, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

3. Hard Surface Compositions

The articles of the present invention can comprise from no more than about 1600 weight percent of a cleaning paste based on the weight of the substrate, preferably comprise no more than about 1000 weight percent, more preferably no more than about 800 weight percent, and still more preferably no more than about 600 weight percent cleaning paste based on the weight of the substrate. Generally the hard surface composition will preferably comprise at least 15 weight percent, preferably at least 25 weight percent, more preferably at least 50 weight percent, and still more preferably at least 60 weight percent cleaning paste based on the weight of the substrate. The articles of the present invention preferably comprise at least about 4.5 grams of said cleaning paste.

The cleaning paste preferably comprises a surfactant or a mixture thereof. Preferably, said surfactant is selected from the group consisting of anionic surfactant, amphoteric surfactant, nonionic surfactant, zwitterionic surfactant, and mixtures thereof.

Suitable anionic surfactants for use in the compositions herein include any known anionic surfacant suitable for use in dishwashing. More preferably said anionic surfactants include water-soluble salts or acid sulphatse, sulphonates or carboxylates. More preferably said anionic surfactants have the formula $ROSO_3M$ wherein R preferably is a $C_6$-$C_{20}$ linear or branched hydrocarbyl, preferably an alkyl or hydroxyalkyl having a $C_{10}$-$C_{20}$ alkyl component, more preferably a $C_{10}$-$C_{14}$ alkyl or hydroxyalkyl, and M is H or a cation, e.g., an alkali metal cation or ammonium or substituted ammonium, but preferably sodium.

Amphoteric surfactants are preferred additional surfactants. The amphoteric surfactants useful in the present invention are preferably selected from amine oxide surfactants containing one alkyl moiety of from about 10 to about 18 carbon atoms and about 2 moieties selected from the group consisting of alkyl groups and hydroxyalkyl groups containing from about 1 to about 3 carbon atoms. Preferred amine oxides include $C_{10}$-$C_{18}$ alkyl dimethyl amine oxides and $C_8$-$C_{12}$ alkoxy ethyl dihydroxy ethyl amine oxides.

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Said nonionics include the condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol. Alternative preferred nonionic surfactants include the alkylpolyglycosides having the formula

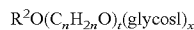
$$R^2O(C_nH_{2n}O)_t(glycosl)_x$$

wherein $R^2$ is selected from the group consisting of alkyl, alkyl-phenyl, hydroxyalkyl, hydroxyalkylphenyl, and mixtures thereof in which the alkyl groups contain from about 10 to about 18, preferably from about 12 to about 14, carbon atoms; n is about 2 or about 3, preferably about 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Optional Ingredients

The hard surface compositions of the present invention may comprise one or more additional skin care components. In a preferred embodiment, where the compositions are to be in contact with human keratinous tissue, the additional components should be suitable for application to keratinous tissue, that is, when incorporated into the composition they are suitable for use in contact with human keratinous tissue without undue toxicity, incompatibility, instability, allergic response, and the like within the scope of sound medical judgment.

The *CTFA Cosmetic Ingredient Handbook*, Second Edition (1992) describes a wide variety of nonlimiting cosmetic and pharmaceutical ingredients commonly used in the personal care industry, which are suitable for use in the compositions of the present invention.

In any embodiment of the present invention, however, the additional components useful herein can be categorized by the benefit they provide or by their postulated mode of action. However, it is to be understood that the additional components useful herein can in some instances provide more than one benefit or operate via more than one mode of action. Therefore, classifications herein are made for the sake of convenience and are not intended to limit the active to that particular application or applications listed.

Bleaching Agent

Another optional ingredient of the present composition is a bleaching agent. Any bleach known for detergent use may be used, as approporiate. Preferred bleaches include a peroxy carboxylic acid bleach or a hydrophilic precursor thereof. Preferably pemonanoic acid, n-nonanoyl-6-aminopercaproic acid, diperoxydodecane dioic acid, and phthalimidoperoxyhexanoic acid (PAP). Other preferred aromatic bleaches are substituted perbenzoic acids (e.g. meta-chloroperoxybenzoic acid, magnesium monoperoxyphthalate). The bleach system may also comprise other components such as bleach activators or catalysts to boost the action of the bleach as necessary.

Other useful bleaches include hydrophobic bleach compound. Examples are diacyl peroxides, (e.g. benzoyl peroxide), di-alkyl peroxides (e.g. di-tert-butyl peroxide), and peroxyesters (e.g. tert-butyl peroxy acetate).

The total amount of bleach in the composition applied to the substrate can range from 1 to 30%, preferably 3 to 20%, by weight of composition.

Water Transfer Agent

The composition may also comprise a water transfer agent which acts as a structurant. Suitable water transfer agents are particulate materials that are capable of absorbing free water from the composition, in particular free water associated with surfactant and/or bleach. We find that the presence of such water transfer agents or structurants has the further benefit that release of surfactant and bleach from the composition into the aqueous cleaning environment is controlled.

The water transfer agent is capable of withdrawing water from the surfactant. By "capable of withdrawing water from the surfactant" it is meant that there is a greater affinity between water and the water-transfer agent than there is between water and the surfactant.

The water-transfer agent is selected from the group consisting of inorganic oxides and salts, especially hydratable oxides and salts, in particular oxides and salts of silicon, aluminium, zinc, boron, phosphorus, alkaline earth metals and alkali metals and mixtures thereof. Examples include silicates, silicic acid and silica, citric acid, citrates, sodium and potassium tripolyphosphates, sodium and potassium sulfates, magnesium and calcium sulfates. Preferably, the water-transfer agent is selected from the group consisting of silica, salts of magnesium and mixtures thereof.

More preferably the water-transfer agent is silica, preferably amorphous fumed silica. Hydrophobic silica does not act as water transfer agent as it does not possess the necessary hydrophilicity.

Preferably the water transfer agent has surface area measured by BET (described in DIN 66131 and as originally described in JACS, Vol. 60, 1938, p309 by Brunauer, Emmet and Teller) of from 5 to 800 $m^2/g$. More preferably the water-transfer agent has a surface area of from 100 to 400 $m^2/g$.

The silica can have an average particle size of from 0.05 to 1 μm, preferably from 0.2 to 0.3 μm. When present the composition applied to the substrate comprises from 2.5 to 15% water-transfer agent, more preferably 5 to 10% and still more preferably about 6%.

Test Methods

Steady Lather Volume Test

Articles of the present invention provide a steady lather profile as described hereafter. The lathering cleansing articles have high Total Steady Lather Volumes, whereas the non-lathering articles have low Steady Flash Lather Volumes. The personal care article can be cleansing or non-cleansing, and can be lathering or non-lathering with different lather profiles as described below. The Steady Lather Volume Test provides a measure of the lather profile of an article in the presence of a renewed water supply, a condition such as naturally exists during bathing or showering.

The lather profile described herein is a combination of the Steady Flash Lather Volume and the Steady Total Lather Volume, both of which are determined in accordance with the following Steady Lather Volume Test. Eight 1,000 ml graduated cylinders are chosen which are marked in 10 ml increments and have a height of 14.5 inches at the 1,000 ml mark from the inside of the base (for example, Pyrex No. 2982). 100 grams of distilled water (+/−0.3 grams, at 23° C.) is added to each graduated cylinder. The cylinders, numbered sequentially from the first cylinder (Cylinder 1) to the last cylinder (Cylinder 8) are clamped in a rotating apparatus which clamps the cylinders with an axis of rotation which transects the center of the graduated cylinder in an axis parallel to the ground with the cylinder standing upright. Stopcocks are added to Cylinder 2 through Cylinder 8.

The article is prepared by folding it into four equal width strips in the longest dimension. If folding and inserting into the graduated cylinders is not possible due to size of the article, the article is cut into strips that can be inserted, and any contents which may spill out during this procedure are caught and added separately into the first graduated cylinder described hereinafter. These strips are stacked and clipped at one end with a simple binder clip, which is selected to be narrow enough to fit inside the neck of the graduated cylinders. A thin polymer thread such as a thin fishing line is tied to the clip so that when the thread is held aloft, the strips hang vertically from the clip and thread. The strips are inserted into the first graduated cylinder (Cylinder 1) so that they hang vertically inside the graduated cylinder with the top ends of the stack of strips hanging evenly with the 1,000 ml mark on the side of Cylinder 1.

The stopcock is then inserted into the neck of Cylinder 1, fixing the strips of the article relative to the graduated cylinder. If necessary, the overhanging thread can be taped to the outside of Cylinder 1 before inserting the stopcock. Also, to prevent leaking, Teflon® tape can be used to effect a waterproof seal. The cylinders are automatically rotated by the rotating apparatus 50 rotations at a steady rate of 50 rotations in 88 seconds in order to generate a lather, which is comprised of foam cells, and stopped in a vertical position to complete a first rotation sequence.

A timer is set to allow 30 seconds for the lather thus generated to drain. After 30 seconds of such drainage, the first lather volume, designated Lather in Cylinder 1, is measured to the nearest 10 ml mark by recording the lather height in ml up from the base in Cylinder 1 (said height includes water that has drained to the bottom, on top of which the lather is floating). If the top surface of the lather is uneven, the lowest height at which it is possible to see halfway across the first graduated cylinder is the Lather in Cylinder 1 (ml). If the lather is so coarse that a single or only a few foam cells reach across the entire cylinder, the height at which at least 5 foam cells are required to fill the diameter is the Lather in Cylinder 1, also in ml up from the base. Foam cells larger than one inch in diameter are designated as unfilled air instead of lather when they occur at the top surface of the lather. Lather that collects on the top of the graduated cylinder but does not move to the bottom of the graduated cylinder is also incorporated in the measurement of the lather on the top is in its own continuous layer, by adding the ml of foam collected there using a ruler to measure thickness of the layer and translating it to ml of volume, to the ml of lather measured up from the base. If a significant amount of lather (e.g., about 60 ml of volume or more) hangs on the side of the graduated cylinder making measurement of the total lather inaccurate or difficult, the lather on the top and sides is urged to the bottom part of the graduated cylinder to meet the other lather prior to measuring volume (during the 30 second drainage period) using a semi-circular shaped flexible plow attached to a rod, for example a 2 inch diameter plug cut from a sponge, cut again in half, and secured to a long threaded rod. The maximum lather volume possible is 1,000 ml (even if the total foam height exceeds the 1,000 ml mark on the graduated cylinder). The minimum lather volume possible is 100 ml (even if there is no foam, the height of the water in the graduated cylinder is designated the top of the lather and is measured as the Lather in Cylinder 1).

After the Lather in Cylinder 1 is recorded, the thread is held and stopcock removed, and the article is removed from the first graduated cylinder, which is then re-cocked. Holding the article only by the thread, the strips are lightly touched for a few seconds to a stack of absorbent paper towels to remove water drops from the bottom of the strips. Then, in the same manner as previously described, the strips of the article are fixed inside the second graduated cylinder, which is numbered as previously described as Cylinder 2, its stopcock is added, and a second rotation sequence is completed, the lather volume being measured in the second cylinder in the same manner as described for the first graduated cylinder, and is recorded as the Lather in Cylinder 2. This sequence is continued a total of eight times, the lather volume in each graduated cylinder being recorded as the lather volume in that cylinder. That is, the lather volume in Cylinder 1, Cylinder 2, Cylinder 3, Cylinder 4, Cylinder 5, Cylinder 6, Cylinder 7 and Cylinder 8 is designated, respectively, as the Lather in Cylinder 1, Lather in Cylinder 2, Lather in Cylinder 3, Lather in Cylinder 4, Lather in Cylinder 5, Lather in Cylinder 6, Lather in Cylinder 7, and Lather in Cylinder 8. The Steady Flash Lather Volume is obtained by adding together the Lather in Cylinder 1 and the Lather in Cylinder 2. The Steady Total Lather Volume is obtained by adding together the lather obtained in all eight graduated cylinders.

Immersion Density Method

Substrate materials for use in articles described herein have preferred density ranges contributing to both improved handleability and reduced scratchy feel against the skin. The densities of the articles or layers of the present invention comprising foams, especially closed cell foams, can be determined using the Immersion Density Method.

Density of foam webs with a substantially closed structure, e.g. many foams, is measured by buoyancy in a fluid of known density, which is excluded from the interior structure of the web foam during the measurement. Water is used as the immersion fluid, having a density of 1.00 gm/cm$^3$.

About 500 ml of water is placed in a clear-walled beaker, for example a glass, 800 ml beaker, and allowed to stand (covered) to de-aerate for 1 day. The beaker containing water is placed on an analytical balance, and the balance is zeroed. A stand with a height adjustable arm is placed near the balance with the movable arm in a horizontal position over the beaker, but not contacting the beaker. A rigid immersion wire is fixed to the horizontal arm in a vertical position, for example a 1 mm diameter metal wire. A segment of a web is cut which is small enough to fit inside the beaker without contacting the walls of the beaker, but large enough to provide accurate results, i.e., a segment of about 8 square inches in area. An analytical balance is used to determine its weight, $W_1$.

The cut web segment is fixed on the bottom of the immersion wire by penetrating a portion of the web in the center of the segment, then slowly immersing the web in the water of the beaker without entrapping air bubbles, and without contacting the edges or bottom of the beaker, by moving the height adjustable arm of the stand downward. When the web segment is completely immersed, the height adjustable arm is clamped so that everything is stationary with the web segment completely immersed and not in contact with the beaker nor the top surface of the water. The weight reading on the balance is recorded, which is the buoyancy of the web segment, $W_2$. If the reading on the balance does not stabilize, the weight after 5 seconds immersion is recorded as the buoyant force, unless the instability is caused by transient surface bubbles which are removed by reimmersion or tapping the beaker sides.

The influence of the wire volume is measured by separately zeroing the balance with the beaker containing immersion fluid on the balance, immersing the wire only to the same depth as during the substrate buoyancy measurement, clamping the wire to the stand, and reading the buoyant force from the wire as the weight on the balance, $W_3$. $W_3$ should be small relative to $W_2$. The Immersion Density is calculated according to Equation 4:

$$\text{Immersion Density} = [W_1/(W_2-W_3)] \times \rho_f \quad \text{Equation 4}$$

where $\rho_f$ is equal to 1.00 grams per cubic centimeter. Several segments of web are measured until a reliable average result is obtained. For composite materials, the density of a foam component can be measured by removing a portion of the composite and measuring it. Also, the individual component densities of a composite which includes a foam may be algebraically determined by measuring the composite density by the immersion method described herein, and apportioning the weight and volume contribution to the individual components using known or measured basis weight and densities of resins, fibers, or object features of the composite.

Calculated Density, Low Pressure Thickness and Basis Weight Methods

Thickness of an object, which can be a web, article, composite, domain, substrate or article is obtained using a Mitutoyo Corporation Digital Disk Stand Micrometer Model Number IDS-1012E or similar (Mitutoyo Corporation, 965 Corporate Blvd, Aurora, Ill., USA 60504). The micrometer has a 1 inch platen weighing about 32 grams, which measures Low Pressure Thickness at an application pressure of about 40.7 grams per square inch (gsi) (6.32 gm/cm$^2$). The digital gauge is electronically zeroed to begin with the platen at rest on the base. The Low Pressure Thickness is measured by raising the platen, placing a section of the object on the base beneath the platen, carefully lowering the platen to contact the substrate, releasing the platen, and measuring the Low Pressure Thickness in mm on the digital readout. The object should fully extend to all edges of the platen to make sure thickness is measured at the lowest possible surface pressure, except for the case of rigid substrates which are not flat. For rigid objects which are not completely flat, a flat edge of the object can be measured using only one portion of the platen impinging on the flat portion of the object. Alternately, flat portions of the object can be cut and inserted under the platen to measure their thickness.

Basis weight is measured by weighing an object (article, layer, composite, web) of known area and dividing its weight by area in gsm (grams/meter$^2$).

Calculated Density is determined from Equation 5 and is expressed in units of grams per cubic centimeter (grams/cm$^3$).

$$\text{Calculated Density} = \text{Basis Weight}/(\text{Low Pressure Thickness} \times 1{,}000) \quad \text{Equation 5}$$

(Basis Weight in gsm; Low Pressure Thickness in mm.)

When the foam is a composite comprising another web or webs or web-like elements (fibers, e.g.), and the web or webs existed as a prior web or webs having a basis weight, the basis weight of the foam layer is the basis weight of the composite (gsm) minus the sum of the prior basis weights of the other web or webs.

When the foam comprises other chemical or non-chemical components in a miscible or immiscible mixture or blend with the foam, and the amount of the other components expressed as grams of dry (evaporated) solids per square meter area of web or article is known or can be determined, then the basis weight of the foam is the total (dry, evaporated) basis weight minus the weight of the other components expressed in the same units (gsm).

Compressed Thickness Method

The compressed thickness of a substrate, layer, composite, film, nonwoven or article is measured using a Cady Micrometer (dial type) Model M (EJ Cady & Co, Wheeling, Ill., USA) which measures thickness using a pressure between 7-9 psi with a ⅝ in. diameter contact area, in mils (1/1000 in.), the result being converted to mm by multiplying by the result in mils×25.4 nm/1,000 mil. Thickness is measured in multiple areas of an article to obtain a representative average. The upper piston is lowered slowly onto the target to avoid crushing the article, and equilibrium thickness after a few seconds at rest is measured. For each measurement, the thickness is measured to the nearest 1/10 mil, estimating the tenth place according to position on the dial gauge.

Abrasiveness Value Methodology

The Abrasiveness Value indicates the "non-scouring" property of the extruded foam layer of the present articles. The extruded foam layer of the present invention are exfoliating but are not rough to the skin. Therefore, the Abrasiveness Value determination involves rubbing the extruded foam layer along a test surface using a mechanical device and then examining the resulting scratch marks produced on the test surface using different analysis techniques.

The following equipment is needed for the methodology.
1. Martindale Toothbrush Wear and Abrasion Tester: Model 103, serial nos. 103-1386/2 upwards. Martindale 07-01-88 made by James H. Heal and Co. Ltd. Textile Testing and QC Equipment. Foot area: 43×44 mm. 1 Kg weight.
2. Capped Polystyrene strips 11×8 cm. Clear general purpose polystyrene layer on white High Impact Polystyrene eg. EMA Model Supplies SS-20201L.
3. Substrates to be tested.
4. Glossmeter e.g. Sheen Tri-Microgloss 20-60-85

Prepare the polystyrene strips for scratching by removing plastic protective coating from the side to be scratched and rinsing with ethanol (do not use tissue). Place the strip onto non abrasive surface and allow strip to dry in the air. Then, attach the polystyrene strip to the base of a Martindale wear tester with tape along the edges. Align the strip centrally under the path of the scrubbing device, with the length of the strip in the direction of movement. Cut a 2.5"×2.5" substrate sample. Attach the substrate sample to the scrubbing foot of the Martindale wear tester, with double sided tape, aligning the machine direction of the substrate with the direction of travel. Secure the scrubbing foot assembly into the instrument with the screws supplied. Slot 1 Kg weight on to the top of the scrubbing foot assembly and ensure the scrubbing foot moves only in one direction (forward and backwards). Cover the entire Martindale wear tester with a safety screen. Set the machine to perform 50 cycles in 1 minute and allow to run. (Frequency=0.833 Hz). Once the machine has stopped take off the footer assembly and lift the polystyrene strip off the base of the machine. Label the polystyrene indicating the substrate used and store in a plastic bag.

Next, the strips are analyzed. The strips are placed on a black construction paper background and at least 5 samples of the same substrate are analyzed to get a reproducible average. The Glossmeter is placed orthogonally (such that light beam is at right angles to scratches) and centrally over the scratched side of the polystyrene strip. A 20° angle is selected and the sample is measured yielding the Abrasiveness Value. As the Abrasiveness Value decreases the scratchiness or scouring property of a substrate increases.

Friction Coefficient Method

Preferably articles of the present invention have a friction coefficient that allows them to move easily on the skin or other surface being cleansed during their use. More preferably, the articles have friction coefficients on the two sides that differ by a sufficient amount such that the article can be used with a low friction side against the skin or other surface being cleansed to enhance ease of movement across the skin while affording an improved ability to grip the top surface without slipperiness.

Friction coefficient is measured using a Texture Analyzer TA-xt2i (Texture Technologies, Scarsdale, N.Y., USA) using a 5 kg load cell and a measurement apparatus comprising a bottom layer, a friction sled, a weight, and a thin line with a clip. A friction sled is connected to the Texture Analyzer grip using thin line (10 lb. test nylon fishing line, e.g.) connected through a pulley so that as the Texture Analyzer head moves upwards in tension mode, the sled is dragged horizontally. Frictional losses across the pulley and due to bending of the line should be minimal.

Teflon in sheet form is used as the bottom layer. A smooth, adhesive backed skived Teflon® sheet having a basis weight of 38 grams per square foot including the adhesive layer (but not the release paper backing) is adhered to a flat plastic surface, rolling to ensure no air bubbles are entrapped. This bottom layer measures about 14 inches long, the machine direction of the Teflon® sheets aligned with the long direction of the bottom layer, which is also the direction of movement of the friction sled comprising the article. The bottom layer is placed alongside the Texture Analyzer so a sled can be dragged along the length of the sheet when the Texture Analyzer is operated in tension mode. A sled is prepared which is a crosslinked silicone foam having a basis weight of about 1900 gsm, a Low Pressure Thickness of about 3.56 mm, a Cady Thickness (8 psi) of about 131.5 mils, and a 3 Point Bending rigidity (slope) of about 12.8 g/cm/cm. The sled is a square about 88 mm on edge with rounded corners, and weighs about 34 grams. The line is run through the pulley, a clip attached to its trailing end, and is clipped onto the sled. A 400 gram weight with a 60 mm diameter footprint is placed atop the sled, the sled sitting on the Teflon sheet coated bottom layer. The friction coefficient of the side of an article to be measured is placed between the sled and the bottom layer, covering the sled. If the article is smaller than the sled and insufficiently thick to keep the sled from dragging on the bottom layer, the sled is cut smaller. The article is clipped to the sled on the leading edge (relative to the direction of motion) so that the article will not move relative to the sled during measurement, preferably by wrapping the article over the leading edge of the sled prior to clipping it into position, with the side to be measured against the bottom layer. The 400 gram weight is placed on the sled in a position as close to the leading edge as possible without interfering with the clip, and in a position so that the clip does not drag against the Teflon coated bottom layer during the measurement. A measurement is commenced by pulling the sled at a rate of 1.0 cm/second until the sled reaches the edge of the bottom layer. Force/distance data are collected by the Texture Analyzer. The average force data when the measurement reaches a steady value is recorded as the friction force in grams, of the substrate layer in contact with the bottom Teflon coated layer. If the friction does not reach a steady value, the average force over the middle third of the measurement period is taken as the friction value.

The friction coefficient is calculated in the conventional manner, as the ratio of the friction force (i.e., the recorded friction value in grams) to the normal force. The normal force is 434 grams, the weight of the article being ignored if it is less than about 15 grams.

The article is then turned over, reattached to the sled, and the measurement repeated with the opposite side of the article against the Teflon bottom layer. The Teflon bottom layer is cleaned between each measurement with solvent, and dried.

In addition to measuring the friction coefficient of dry articles, as indicated, the friction coefficient can be measured wet, by placing the article on the bottom layer and pouring an excess of room temperature distilled water on the article until it absorbs as much water as possible, but without movement so that lathering does not occur, and measuring the friction coefficient as before. In addition, friction can be measured in the presence of lather for an article by wetting the article, creating an excess of lather by rubbing the wetted article against itself, placing the article on the measurement apparatus with excess lather on the article surface, placing the sled and weight as before, and running the measurement as before. The friction coefficient of both sides of articles is measured dry, wet, and lathered. When the sides are the same, the friction coefficient is the average of the results for the two sides. A sufficient number of repetitions are run on different samples of the same article to obtain a representative average. The difference in friction coefficient of the two sides under dry, wet and lathered conditions is determined by subtracting the average value for the friction coefficient for one side from the other, and taking the absolute value of the result.

When the articles are tested dry or wet, preferably the difference in friction coefficient between the two sides is at least 0.02 units, more preferably the difference is at least 0.03 units, even more preferably the difference is at least 0.04 units, and most preferably the difference is 0.05 units or greater.

When the articles are tested lathered, preferably the difference in friction coefficient between the two sides is at least 0.01 units, more preferably the difference is at least 0.02 units, even more preferably the difference is at least 0.03 units, and most preferably the difference is 0.04 units or greater.

Moisture Retention Methodology

As described above, the articles of the present invention can be "substantially dry". The Moisture Retention is indicative of the dry feel that users perceive upon touching the articles of the present invention as opposed to the feel of "wet" wipes.

In order to determine the Moisture Retention of the present articles and other disposable fibrous, non-woven web-based products, the following equipment and materials are needed.

| | |
|---|---|
| Bounty White Paper Towel | Procter & Gamble SKU 37000 63037 Basis Weight = 42.14 gsm |
| Balance | Accurate to 0.0 g |
| Lexan | 0.5" thickness large enough to cover samples completely and weighs 1000 g |
| Weight | A 2000 g weight or combination to equal 2000 g |

Next, weigh two paper towels separately and record each weight. Place one paper towel on flat surface (e.g., lab bench). Place the sample article on top of that towel. Place the other paper towel on top of sample article. Next, place the Lexan and then the 2000 g weight(s) on top of the sandwiched sample article. Wait 1 minute. After the minute, remove weight(s) and Lexan. Weigh the top and bottom paper towel and record the weight.

Calculate the Moisture Retention by subtracting the initial paper towel weight from the final weight (after 1 minute) for both the top and bottom paper towels. Add the weight differences obtained for the top and bottom paper towels. Assuming multiple articles are tested, average the total weight differences to obtain the Moisture Retention.

As described above, the articles of the present invention can be "substantially dry", "moist", or "wet" prior to use. The article can feel dry to the touch and still contain high water content. The Moisture Retention is indicative of the dry feel that users perceive upon touching the articles of the present invention as opposed to the feel of "wet" articles. Thus, articles of the present invention that feel dry to the touch can have a dry feel relatively independent of the amount of water they contain. Articles of the present invention which have a dry feel will exhibit a Moisture Retention of less than about 0.95 gms, preferably less than about 0.75 gms, even more preferably, less than about 0.5 gms, even more preferably less than about 0.25 gms, even still more preferably less than about 0.15 gms, and most preferably, less than about 0.1 gms.

As described above, the articles of the present invention can be "wet" prior to use. The article can feel wet to the touch and contain high water content. The weight percent of liquid in the "wet" article is based on the dry weight of the web. The weight is expressed as a weight of the total composition. Thus, the "wet" articles of the present invention will generally comprise from about greater than 40% by weight of water, preferably from 40% to about 95% by weight of water, and more preferably from about 50% to about 80% by weight of water.

Methods of Cleansing the Skin or Hair

The present invention also relates to a method of cleansing the skin or hair with a personal cleansing article of the present invention. These methods comprise the steps of wetting with water a substantially dry, disposable, personal cleansing article comprising a substrate having a extruded foam layer, a lathering surfactant, and optionally a conditioning component, and contacting the skin or hair with such wetted article. In further embodiments, the present invention is also useful for delivering various benefit agents to the skin or hair.

The articles of the present invention are preferably substantially dry and are intended to be wetted with water prior to use. The article is wetted by immersion in water or by placing it under a stream of water. Lather is generated from the article by mechanically agitating and/or deforming the article either prior to or during contact of the article with the skin or hair. The resulting lather is useful for cleansing and conditioning the skin or hair. During the cleansing process and subsequent rinsing with water, the conditioning agents and benefit agents are deposited onto the skin or hair. Deposition of conditioning agents and active ingredients are enhanced by the physical contact of the substrate with the skin or hair.

Without being limited by theory it is believed that the substrate significantly contributes to generation of lather and deposition of conditioning agents and any other benefit agents. It is believed that this increase in lathering and deposition is the result of the surface action of the substrate. As a result, milder and significantly lower amounts of surfactants may be employed. The decreased amount of required surfactant is believed to relate to the decrease in the drying effect of the skin or hair by the surfactants.

The substrate also enhances cleansing. The presence of the extruded foam layer can increase rigidity and thickness of the article. Additionally, the substrate can have differing textures on each side, e.g. a rough side and a smooth side. The extruded foam plus the addition of differing textures on each side of the substrate acts as an efficient lathering and exfoliating implement. The foam also aids in preventing crushing and crumpling of the article during use. By physically coming into contact with the skin or hair, the extruded foam plus the subtrate significantly aids in cleansing and removal of dirt, makeup, dead skin, and other debris.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total cleansing, treatment compositions, unless otherwise specified.

Example 1

A closed cell extruded polyethylene foam can be prepared which is a ⅛ inch nominal thickness flat foam sheet web with a 1.5 pounds per cubic foot (pcf) nominal density, and is prepared by extruding low density polyethylene (LDPE) resin with a hydrocarbon blowing agent. The foam web is slit in the machine direction in rows, the slits ¾ in. long with ¼ in. between slits within a row, and ⅛ in. between rows of slits. Slits in alternating rows are offset in the MD by ½ the length of a slit, so that when the slitted web is pulled apart in the CD, the web opens to a lattice pattern. The foam is supplied by Kevron LLC, Portland, Oreg., USA. The web has a Low Pressure Thickness of 3.08 mm and a Basis Weight of 105 gsm. The Calculated Density is 0.034 gm/cm$^3$ and the Immersion Density is 0.0356 gm/cm$^3$. The web has a Rigidity in the MD of 11.6 gm/cm$^2$, and a Rigidity in the CD of 0.20 gm/cm$^2$. High density polyethylene resin (HDPE) can be mixed with the LDPE or substituted entirely to increase the rigidity.

Example 2

A closed cell extruded polyethylene foam can be prepared which is a ¹⁄₁₆ inch nominal thickness flat foam sheet web with a 1.5 pcf nominal density, and is prepared by extruding low density polyethylene (LDPE) resin with a hydrocarbon blowing agent. The foam web is slit in the machine direction in rows, the slits ¾ in. long with ¼ in. between slits within a row, and ⅛ in. between rows of slits. Slits in alternating rows are offset in the MD by ½ the length of a slit, so that when the slitted web is pulled apart in the CD, the web opens to a lattice pattern. The foam is supplied by Kevron LLC. The web has a Low Pressure Thickness of 1.98 mm and a Basis Weight of 56 gsm. The Calculated Density is 0.028 gm/cm$^3$ and the Immersion Density is 0.0346 gm/cm$^3$. The web has a Rigidity in the MD of 2.1 gm/cm$^2$, and a Rigidity in the CD of 0.05 gm/cm$^2$.

Example 3

A closed cell extruded polypropylene foam can be prepared which is a 0.6 pcf nominal density foam. The foam is a sheet with ripples extending in the MD having a periodicity of about 12 mm. The foam is supplied by Pactiv Corp, Lake Forest, Illinois, USA under the trade name Microfoam® MF045. The foam has a Low Pressure Thickness of 0.66 mm, a Cady Thickness of 0.55 mm, a Basis Weight of 12 gsm, a Calculated Density of 0.018 gm/cm$^3$, an Immersion Density of 0.014 gm/cm$^3$, a Rigidity in the MD of 0.28 gm/cm$^2$, and a Rigidity in the CD of 0.06 gm/cm$^2$, a Cell Size in the MD of between 0.79 mm and 0.93 mm for several lots of the foam, and a Cell Size in the CD of between 0.56 mm and 0.65 mm for several lots of the foam.

Example 4

A closed cell extruded foam can be prepared which is an extruded polyethylene foam. The foam is a lattice of ropes extruded as dual concentric cylinders with an inner and outer series of ropes, each rope about 4 mm diameter and extruded at about 20° off the cylinder axis, defining about a 40° angle of the ropes between the inner and outer ring of ropes. The ropes are attached, welded at all contact points during processing while in the melt state. The cylinder is sliced in the MD to prepare a flat web. The Basis Weight is measured without compression of the lateral dimensions of the flat web, and is about 114 gsm. The lattice foam web has a Low Pressure Thickness of 6.35 mm, a Cady Thickness of 2.26 mm, an Immersion Density of 0.018 gm/cm$^3$, a Rigidity in the MD of 5.50 gm/cm$^2$, and a Rigidity in the CD of 0.20 gm/cm$^2$.

Example 5

A batting layer can be obtained which is an airlaid blend of carded fibers (50% PET, 50% PE/PP core-sheath bicomponent) having a basis weight of 65 gsm and a Low Pressure Thickness of about 2.7 mm, from Libeltex Nev., Belgium. The batting layer has a MD Rigidity of about 0.41 gm/cm/cm and a CD Rigidity of about 0.08 gm/cm/cm.

Example 6

A batting layer can be obtained which is an airlaid, carded web of 6 denier polyester fibers which is bonded with about 10% adhesive, by weight of the web. The batting layer has a Basis Weight of about 60 gsm, a Low Pressure Thickness of 2.8 mm, a MD Rigidity of about 0.12 gm/cm$^2$, and a CD Rigidity of about 0.037 gm/cm/cm. The web is manufactured by Stearns, Inc., Cincinnati, Ohio, USA.

Example 7

A fibrous nonwoven web can be obtained which is 100% polypropylene fibers prepared by a spunbond/spunlace process, having a basis weight of 50 gsm, and is manufactured by Avgol Nonwovens, Greensboro, N.C., USA.

Example 8

A nonwoven web can be obtained which is a core-sheath bicomponent fiber (PE/PP) spunbond web having a basis weight of 46 gsm, manufactured by BBA Nonwovens, Simpsonville, N.C., USA.

A lathering surfactant composition can be prepared and can be used in the following examples. The surfactant composition can be prepared using the following ingredients. The ingredients are prepared by mixing the cationic polymer with the glycol and surfactants under heat with continuous stirring to avoid lumps. Foaming is avoided. The perfume is added during cooling. The lathering surfactant composition melts upon heating to about 60 degrees C. or more, and solidifies upon cooling to a hard solid. The percentages added in this and subsequent examples are of the ingredient including water it may contain.

| Ingredient | Supplier or common CTFA name | Amount of Ingredient added |
| --- | --- | --- |
| Alkyl Glyceryl Sulfonate (AGS) 47.5% solids paste | (Procter & Gamble Co., Iowa City, Iowa, USA) | 62.8% |
| Cocamidopropyl Betaine, 30% active | (Stepan Chemical) AMPHOSOL CG | 19.7% |
| Citric Acid Anhydrous | Citric acid | 0.2% |
| Propylene Glycol | Propylene glycol | 15.2% |
| Polyox WSR-301 | (Amerchol) PEG 90M | 0.20% |
| N-Hance 3196 | (Aqualon-Hercules, Irvine, CA, USA) cationic guar or guar hydroxypropyltrimonium chloride (polymer) | 0.50% |
| Perfume | | 1.0% |
| Preservative & misc. | | 0.4% |

Example 9

A lathering sheet sized article can be prepared for cleansing the body in a shower. The article is prepared by sealing together a first layer which is the web of Example 6, a second, middle layer of the foam web of Example 3, and a third layer of the web of Example 8. Five grams of the surfactant composition is heated and added to the article in five stripes between the first and second layers. The article is sealed in the direction of the stripes, which is the MD, using a pattern of round dots which measure about 6 mm in diameter and which are in rows spaced 20 mm apart. The dots are spaced about 20 mm center to center within rows. The article measures 270 cm² in area. The following properties are measured by flushing the surfactant from the article and measuring the properties of the article in the absence of the surfactant composition. The article is flushed with warm water until the surfactant is essentially gone, while maintaining the article in an unbent position. The article is then lightly pressed with cellulose towels to remove excess water, and dried for about an hour at a temperature of 60 degrees C.

|  | Value |
| --- | --- |
| Low Pressure Thickness | 6.04 mm |
| Thickness Cady | 1.45 mm |
| MD Rigidity | 2.00 gm/cm/cm |
| CD Rigidity | 1.91 gm/cm/cm |

Example 10

A lathering grip sized article can be prepared for cleansing the body in a shower. The article can be prepared by sealing together a first layer which is the web of Example 5, a second, middle layer of the foam web of Example 4, and a third layer of the web of Example 8. The foam lattice web is extended to about twice its original, unstressed lateral dimension prior to sealing. Five grams of the surfactant composition is heated and added to the article in the first and second layers. The article is sealed in the direction of the stripes, which is the MD, using a pattern of round dots which measure about 6 mm in diameter and which are in rows spaced 20 mm apart. The dots are spaced about 20 mm center to center within rows. The article measures 150 cm² in area. The following properties are measured by flushing the surfactant from the article and measuring the properties of the article in the absence of the surfactant composition. The article is flushed with warm water until the surfactant is essentially gone, while maintaining the article in an unbent position. The article is then lightly pressed with cellulose towels to remove excess water, and dried for about an hour at a temperature of 60 degrees C.

|  | Value |
| --- | --- |
| Low Pressure Thickness | 8.67 mm |
| Thickness Cady | 2.23 mm |
| MD Rigidity | 7.0 gm/cm² |
| CD Rigidity | 1.34 gm/cm² |

Example 11

A lathering pad sized article can be prepared for cleansing the body in a shower. The article can be prepared by sealing together a first layer which is the web of Example 7, a second, middle layer of the foam web of Example 1, and a third layer of the web of Example 5. Five grams of the surfactant composition is heated and added to the article in five stripes between the first and second layers. The article is sealed in the direction of the stripes, which is the MD, using a pattern of S-shaped dots which measure about 8 mm long×2 mm wide, the long dimension parallel to the MD, and which are in rows spaced 16 mm apart. The dots are spaced 16 mm center to center within rows. The seal is effected by an ultrasonic sealer. The article measures 11.6 cm×9.2 cm. The following properties are measured. The article is measured with the surfactant composition present and without the surfactant composition present. For the latter, the article is flushed with warm water until the surfactant is essentially gone, while maintaining the article in an unbent position. The article is then lightly pressed with cellulose towels to remove excess water, and dried for about an hour at a temperature of 55 to 60 degrees C.

|  | Value with surfactant | Value without surfactant |
| --- | --- | --- |
| Low Pressure Thickness | 4.19 mm | 5.47 mm |
| Thickness Cady | 1.88 mm | 1.60 mm |
| MD Rigidity | 9.1 gm/cm² | 5.1 gm/cm² |
| CD Rigidity | 0.71 gm/cm² | 0.48 gm/cm² |

Example 12

A lathering pad sized article can be prepared for cleansing the body in a shower. The article can be prepared by sealing together a first layer which is the web of Example 7, a second, middle layer of the foam web of Example 2, and a third layer of the web of Example 5. Five grams of the surfactant composition is heated and added to the article in five stripes between the first and second layers. The article is sealed in the direction of the stripes, which is the MD, using a pattern of S-shaped dots which measure about 8 mm long×2 mm wide, the long dimension parallel to the MD, and which are in rows spaced 16 mm apart. The dots are spaced 16 mm center to center within rows. The seal is effected by an ultrasonic sealer. The article measures 11.6 cm×9.2 cm. The following properties are measured. The article is measured with the surfactant composition present and without the surfactant composition present. For the latter, the article is flushed with warm water until the surfactant is essentially gone, while maintaining the article in an unbent position. The article is then lightly pressed with cellulose towels to remove excess water, and dried for about an hour at a temperature of 55 to 60 degrees C.

|  | Value with surfactant | Value without surfactant |
| --- | --- | --- |
| Low Pressure Thickness | 3.52 mm | 4.57 mm |
| Thickness Cady | 1.67 mm | 1.33 mm |
| MD Rigidity | 4.0 gm/cm² | 2.2 gm/cm² |
| CD Rigidity | 0.43 gm/cm² | 0.25 gm/cm² |

Example 13

An effervescent cleansing pillow grip sized article can be prepared for cleansing the body in the shower. The article can be prepared by sealing together a 65 gsm hydroentangled 70/30 rayon/bico web manufactured by Suominen as the first layer; a microapertured formed film having apertures measuring about 150 microns formed on a 100 mesh wire screen, manufactured by Tredegar, Inc (Terre Haute, Ind., USA).; a third layer which is the same as the second layer and a fourth layer which is the batting of Example 6. Citric acid (2.1 grams) and sodium bicarbonate (2.8 grams) is mixed together and sealed between the second and third layers prior to sealing. The webs are sealed at the perimeter by an electrical impulse sealer which effects a 4 mm wide seal. A small portion of web is left outside the seal to keep the edges from being scratchy. The article is sealed in the center by point bonds in rows 19 mm apart (row to row) and 30 mm apart within a row, the dots having a designed pattern of microdots to add beauty. The lathering surfactant composition is added to the batting interior portion prior to sealing. The article is dried at 120 degrees F. for 24 hours prior to use. The article is measured in the dry state, and then most of the surfactant is flushed off with water for about 10 seconds, the article is blotted lightly to remove water that may drip, and three point bending and Low Pressure Thickness are measured on the wetted article. The article pillows when wet and maintains the loftiness during the measurement. The article measures 13.4 cm long by 11.6 cm wide.

|  | Value for dry article | Value for wetted article |
|---|---|---|
| Low Pressure Thickness | 5.96 mm | 13.65 mm |
| MD Rigidity | 4.4 gm/cm/cm | 7.9 gm/cm/cm |
| CD Rigidity | 1.6 gm/cm/cm | 4.3 gm/cm/cm |

Example 14

A lathering sheet sized article is prepared for cleaning dishes. The article of Example 9 is prepared using a lemon fragrance in the surfactant composition.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable, lathering cleansing article, said article comprising:
   a plurality of substrate layers;
   a cleansing composition; and
   wherein said article is selected from the group consisting of pad sized articles, grip sized articles, sheet sized articles and combinations thereof;
   wherein said pad sized article has an area from about 55 cm$^2$ to about 135 cm$^2$, a rigidity in the Cross Machine Direction (CD) from 0.2 to about 55 gm/cm/cm, a rigidity in the Machine Direction (MD) direction from about 1.0 to about 55 gm/cm/cm and a Low Pressure Thickness from about 2.5 to about 31 mm;
   wherein said grip sized article has an area from about 136 cm$^2$ to about 230 cm$^2$, a rigidity in the Cross Machine Direction (CD) from 0.3 to about 30 gm/cm/cm, a rigidity in the Machine Direction (MD) direction from about 1.6 to about 50 gm/cm/cm and a Low Pressure Thickness from about 1.1 to about 30 mm;
   wherein said sheet sized article has an area from about 231 cm$^2$ to about 500 cm$^2$, a rigidity in the Cross Machine Direction (CD) from 0.15 to about 10 gm/cm/cm. a rigidity in the Machine Direction (MD) direction from about 0.18 to about 30 gm/cm/cm and a Law Pressure Thickness from about 0.40 to about 10 mm.

2. The article of claim 1 wherein at least one layer is selected from the group consisting of nonwovens, wovens, and combinations thereof.

3. The article of claim 2, wherein at least one layer is selected from the group consisting of formed film, batting, extruded foam, and combinations thereof.

4. The article of claim 3, wherein said extruded foam has a Density from 0.0001 gm/cm$^3$ to about 0.25 gm/cm$^3$.

5. The article of claim 3, wherein said extruded foam is selected from the group consisting of polyethylene foams, polypropylene foams, vinyl foams, acrylic foams, polyether foams, polyester foams, polyurethane foams, blends of miscible and immiscible polymers and copolymers, silicone sponge foam, neoprene foams, rubber foams, polyolefin foams and mixtures thereof.

6. The article of claim 3, wherein said extruded foam is selected from the group consisting of open cell, closed cell, double cell, reticulated foams, loaded foams, multiple layer foams and combinations thereof.

7. The article of claim 1, wherein said substrate layer is water insoluble.

8. The article of claim 1, further comprising a cleansing composition associated with said article selected from the group consisting of lathering personal care composition, non-lathering personal care composition, hard surface composition, and mixtures thereof.

9. The article of claim 8, wherein said lathering personal care composition generates a Steady Total Later Volume from about 2200 ml to about 8000 ml.

10. The article of claim 8, wherein said lathering personal care composition generates a Steady Flash Lather Volume from at the least about 1500 ml.

11. The article of claim 8, said lathering personal care composition comprises from about 0.05% to about 1600% by weight of said substrate.

12. The article of claim 8, wherein said lathering personal care composition is selected from the group consisting of anionic surfactant selected from the group consisting of sarcosinates, sulfates, salfonates, isethionates, phosphates, taurates, lactylates, glutarnates, soaps and mixtures thereof; nonionic surfactant is selected from the group consisting of amine oxides, alkyl glucosides, alkyl polyglucosides, polyhydroxy fatty acid amides, alkoxylated fatty acid esters, sucrose esters, and mixtures thereof; amphoteric surfactants selected from the group consisting of betaines, sultaines, hydroxysultaines, alkyliminoacetates, iminodialkanoates, aminoalkanoates, and mixtures thereof.

13. The article of claim 1, further comprising a benefit agent from about 0.05% to about 1600% by weight of said substrate.

14. The article of claim 13, said benefit agent is selected from the group consisting of vitamins, zeolites, peptides, sunscreen actives, terpene alcohols, desquamation actives, anti-acne actives, anti-wrinkle actives, anti-atrophy actives, anti-oxidants, flavanoids, anti-inflammatory agents, anticellulite agents, topical anesthetics, tanning actives, chelators, skin lightening agents, antimicrobial actives, antifungal actives, skin soothing actives, skin healing actives, skin moisturizing actives, cosmetic actives and mixtures thereof.

15. The article of claim 1, further comprising a conditioning agent selected from the group consisting of petrolatum, fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.

16. The article of claim 15, said conditioning agent comprises from about 0.05% to about 1600% by weight of said substrate.

* * * * *